United States Patent [19]

Long et al.

[11] Patent Number: 5,687,093
[45] Date of Patent: Nov. 11, 1997

[54] INTEGRATED SYSTEM FOR GATHERING, PROCESSING, AND REPORTING DATA RELATING TO SITE CONTAMINATION

[75] Inventors: Delmar D. Long, Oak Ridge; Mitchell S. Goldberg, Lenior City; Lorie A. Baker, Oak Ridge, all of Tenn.

[73] Assignee: Lockheed Martin Energy Systems, Inc., Oak Ridge, Tenn.

[21] Appl. No.: 390,350

[22] Filed: Feb. 17, 1995

[51] Int. Cl.$^6$ ................... G06G 7/58; G01N 1/00
[52] U.S. Cl. ........... 364/512; 364/497; 364/498; 364/500; 73/863; 73/864.31; 405/128
[58] Field of Search ............... 364/512, 560, 364/556, 420, 422, 413.38, 474.05, 510, 550, 497, 413.13, 413.22, 500, 498; 33/543, 554, 546, 203, 644, 551, 550; 73/864.43, 151, 38, 40, 73, 84, 154, 19.03–19.05, 863.23, 864.45, 798, 152.11, 863.01, 864.23, 825, 864.21, 864.25; 250/288, 281, 288 A; 356/376; 436/28; 324/323, 345, 348

[56] References Cited

U.S. PATENT DOCUMENTS

| | | | |
|---|---|---|---|
| 4,806,153 | 2/1989 | Sakai et al. | 73/151 |
| 5,010,776 | 4/1991 | Lucero et al. | 73/863.23 |
| 5,063,519 | 11/1991 | Zison | 364/510 |
| 5,150,622 | 9/1992 | Vollweiler | 73/864.74 |
| 5,151,870 | 9/1992 | Beebe et al. | 364/556 |
| 5,246,862 | 9/1993 | Grey et al. | 436/28 |
| 5,316,950 | 5/1994 | Apitz et al. | 436/28 |
| 5,351,532 | 10/1994 | Hager | 73/152.55 |
| 5,359,511 | 10/1994 | Schroeder et al. | 364/413.28 |
| 5,416,321 | 5/1995 | Sebastian et al. | 250/288 |
| 5,435,176 | 7/1995 | Manchak, III | 73/151 |
| 5,435,399 | 7/1995 | Peterson et al. | 73/864.31 |
| 5,497,091 | 3/1996 | Bratton et al. | 324/348 |

OTHER PUBLICATIONS

Ashtech, "GPS Field Surveying Techniques" May 1991.
Tillman, N., "Site Investigation and Remediation with Direct Push Technology", *The National Environmental Journal*, pp. 28–32, Sep./Oct. 1993.
Proceedings, ION Satellite Division's Fifth International Technical Meeting, ION GPS-92 (Sep. 16–18, 1992), Qin, X., Gourevitch, S., Kuhl, M., "Very Precise Differential GPS-Development Status and Test Results".

*Primary Examiner*—Jacques Louis-Jacques
*Attorney, Agent, or Firm*—J. Kenneth Davis

[57] ABSTRACT

An integrated screening system comprises an intrusive sampling subsystem, a field mobile laboratory subsystem, a computer assisted design/geographical information subsystem, and a telecommunication linkup subsystem, all integrated to provide synergistically improved data relating to the extent of site soil/groundwater contamination. According to the present invention, data samples related to the soil, groundwater or other contamination of the subsurface material are gathered and analyzed to measure contaminants. Based on the location of origin of the samples in three-dimensional space, the analyzed data are transmitted to a location display. The data from analyzing samples and the data from the locating the origin are managed to project the next probable sample location. The next probable sample location is then forwarded for use as a guide in the placement of ensuing sample location, whereby the number of samples needed to accurately characterize the site is minimized.

13 Claims, 10 Drawing Sheets

INTEGRATED SYSTEM FOR GATHERING, PROCESSING, AND REPORTING DATA RELATING TO SITE CONTAMINATION

The United States Government has rights in this invention pursuant to Contract No. DE-AC05-84OR21400 between the U.S. Department of Energy and Martin Marietta Energy Systems, Inc.

BACKGROUND OF THE INVENTION (1) Field of the Invention

The present invention relates, in general, to an integrated system for performing site characterization of locations having soil and/or water contamination. More specifically, the inventive integrated system comprises an intrusive sampling subsystem, a field mobile laboratory subsystem, a computer assisted design/geographical information subsystem, and a telecommunication linkup subsystem, all integrated to provide synergistically improved data relating to the extent of site soil/groundwater contamination.

(2) Description of Related Art

Contamination of the environment is a problem that, fortunately, is receiving increasing scrutiny. There are several government mandates, e.g., RCRA, CERCLA, and EPA regulations, which are, at least partially, driving this increased scrutiny. Many of those involved in the environmental field estimate that more than a trillion dollars may be spent on correcting past damage to the environment in the next decade or two. It is estimated that about forty percent of this money will be spent on remediating environmental damage and about sixty percent on site characterization studies.

It is believed that use of the inventive, integrated FAST environmental screening, system will allow the time required to perform a site characterization to be cut by about 60% relative to conventional techniques, and will allow costs to be cut by about 70%, and will increase the probability of accurately determining the existence and extent of an environmental hazard by five times. Additionally, the inventive system reduces the amount of waste generated during field activities and improves worker safety during site characterization activities.

The following hypothetical example will further illustrate the invention's advantages over the prior art. A typical site characterization task might be to determine the horizontal and vertical extent, as well as the chemical characterization, of a groundwater plume. The interface with the plume is 35 feet below the ground surface, the aquifer is 80 feet below the surface, and groundwater flow direction as well as hydraulic gradient is known.

The conventional method would use five separate functions to determine the extent of contamination. Initially, intrusive sampling is generally accomplished by some type of flighted auger or other techniques that drills a hole into the earth, thus allowing for the placement of a sampling conduit—e.g., as per a well. Using the standard "grid" approach (i.e., dividing the area to be sampled into equalized portions), there is a need for about 30 wells placed at three separate depths for a total of 90 wells/sampling points. Once in place, the well is developed, a specified number of well volumes of water are removed, and the well is sampled. The samples are placed in shipping containers and shipped to a fixed based laboratory for analysis.

The second function is the analysis. As noted, this is accomplished in an analytical laboratory somewhere off site to the field effort, and therefore requires the shipping of samples from the field to the laboratory. The constituents of concern in this example could be volatile organic compounds, analyzed using EPA method 8240. This procedure requires the sample be preserved in 0.008% $NaS_2O_3$, and kept at 4° C. Under this process, the samples would have a holding time of 14 days. The estimated cost per sample is $345. Sample results generally become available 4–6 weeks after the last submitted sample.

The third function is the surveying of the wells. The purpose of the survey is to determine the vertical and horizontal position of the well head. This information is vital if a visualization of the projected contamination is to be made, and is used in concert with the information that is generated from the fixed based laboratory. Most frequently, ground-based surveying instruments (e.g., optical-or laser-based) are utilized.

The fourth function is the visual plotting of the test results based on a static contamination condition. This can only be conducted after receipt of analytical and survey data. It should be noted that the ability to accomplish this function in a consistent manner has only became available recently.

The fifth function, in prior art processes, having completed the first four, is to project the next phase of the site characterization—the Phase II. This is accomplished by an interpretation of the available data, along with the implementation of a model projecting plume migration and usually results in a subsequent field investigation and report. In this instance, the static condition seen in the fourth function of Phase I is projected based on a homogenous lithology to determine risk and project status at the time the Phase II data is gathered—i.e., because of the time lags between Phases of the investigation required by the prior art, conventional processes have built-in inaccuracies—e.g., some contaminant plumes can migrate at speeds of about a foot per day.

Against this background, key economics and time factors for a typical, prior art, characterization of a Phase I site may be enumerated. Each well costs about $4000 to install, and about the same to remove. There are 90 of these for a total of about $720,000. Each analytical test costs about $345, two per well, for a total of about $62,100. This excludes the cost of shipping, mobilization and demobilization, etc. The time would be as follows: approximately 75 field days for drilling plus mobilization and demobilization; 28–42 days after receipt of last sample for test results to be submitted; and two weeks of analysis, for a total for Phase I of 116 days. A reasonable estimate of a typical Phase II of a site characterization would be 50% of Phase I in time and value. The totals, then, are approximately $1,500,000.00 and 174 days.

The inventive FAST system also uses the five above described functions. The drilling is usually done using "push" technology, the analysis is accomplished via an onsite laboratory, the surveying is done through satellite vectoring, the position of the plume is visualized daily or twice a day (depending on requirements) using field analytical data in concert with vectored survey information, with plume position projections also being made/displayed at the same frequency.

With the inventive system, typical economics are as follows: sample acquisition costs about $200 per well. There is no cost associated with the removal of the well. The field lab is capable of analyzing 18 datapoint, plus 6 quality check samples per shift using two gas chromatographs. The visual plotting takes place twice a day upon receipt of analytical and survey information. Based on field information, presented in a three dimensional format on a continuing basis, FAST is capable of obtaining required samples for plume delineation using one-third of the sampling points used in traditional systems, due in part to the ability of the process to acquire multiple discrete samples, and is capable of developing 6 sample points per shift. The total field time is 5 days, the "drilling" costs are approximately $10,000, the analysis costs are $15,000, and the daily feedback and plotting costs are $10,000 for a total of about $35,000. 5 field days, and no need for Phase II. As a result of same day feedback of analytical and survey data, site characterization can be completed without the need for a second Phase.

To compare, conventional systems are capable of doing a typical site characterization job for $1.5 million in a period of 174 days. The inventive FAST system is capable of doing the same job for $35,000 and requires a field effort of 5 days. Yet each uses the five noted functions of drilling and sampling, sample analysis, surveying, visualization and feedback. Finally, quality levels favor the FAST system by a significant margin. Results to date have shown that the FAST process is five times more likely to identify the presence of a contaminant than the conventional system. Also, the inventive FAST system is capable of accurately characterizing a contamination site with about one-tenth of the samples used by conventional methods.

SUMMARY OF THE INVENTION

The present invention solves the above-noted problems and avoids the suboptimizations inherent in the prior art by providing an integrated screening system comprising an intrusive sampling subsystem, a field mobile laboratory subsystem, a computer assisted design/geographical information subsystem, and a telecommunications link-up subsystem, all integrated to provide synergistically improved data relating to the extent of site soil/groundwater contamination.

The present invention provides an integrated system of state-of-the-art components that collectively produce a process that insures a low cost, high quality, rapid timeline environmental field screening. The novel combination of components contributes to the invention. The basic components of the integrated system include:

(1) intrusive sampling based on "push" technology for surface, subsurface and groundwater media sampling;

(2) a field mobile laboratory equipped to complement expected site contaminants;

(3) a computer assisted design/geographical information system with data management with interactive three dimensional dynamic graphs presentation capability;

(4) a global positioning system for sample coordinates determination; and (5) a telecommunication linkup for data transmittal and receiving.

Using these components in an integrated fashion, the environmental screening system is designed to determine the horizontal and vertical extent of site soil and/or groundwater contamination with one mobilization of the field investigative team. The system allows for making informed field change decisions concerning site investigation plans on a real time basis, thus assuring minimum field time, minimum cost, and maximum data quality.

BRIEF DESCRIPTION OF THE DRAWINGS

To facilitate understanding of the inventive process and system, reference is made to the appended drawings wherein like numerals refer to like elements throughout, and wherein.

DETAILED DESCRIPTION OF THE PREFERRED EMBODIMENTS

Figure 1:
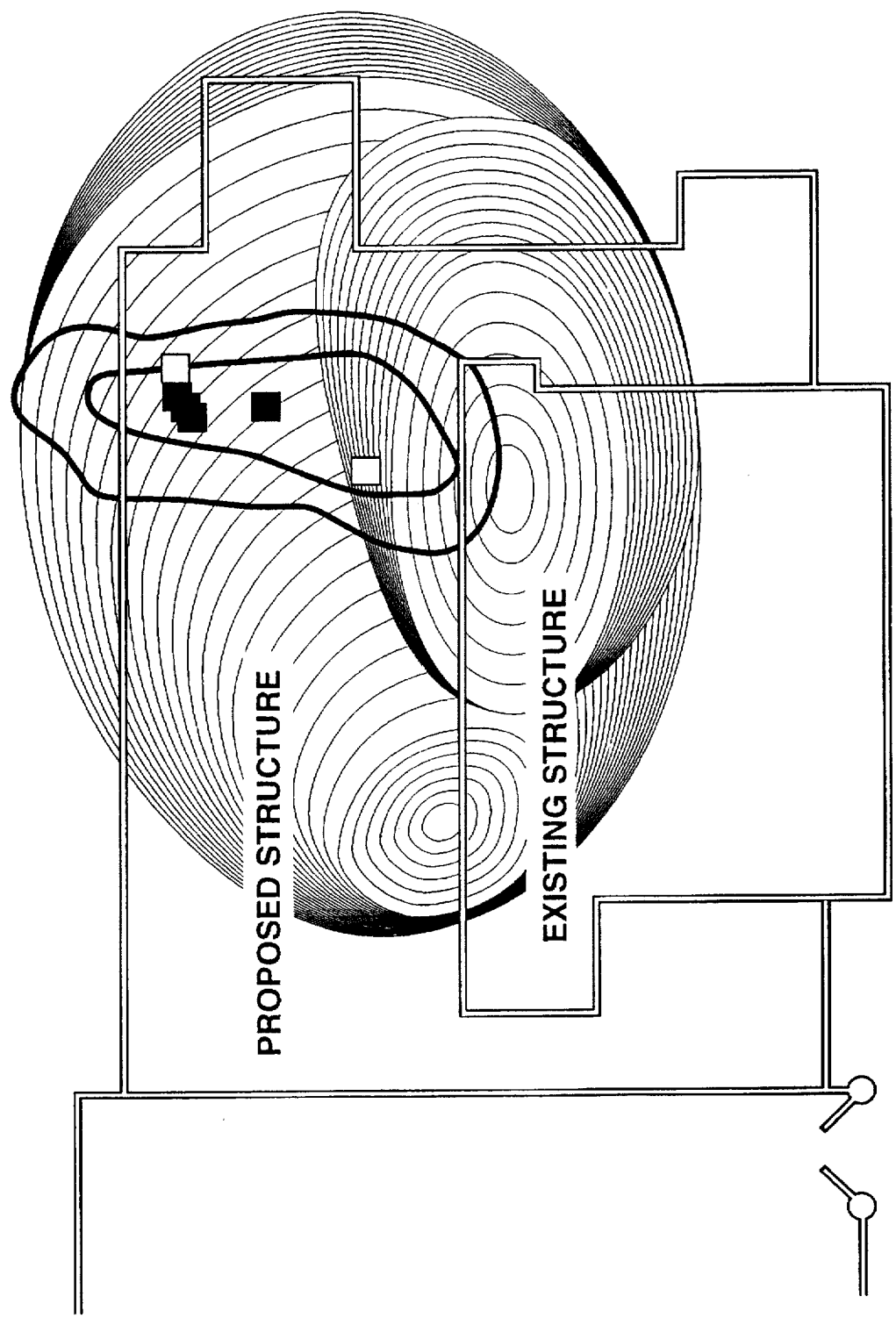
FIG. 1 is a plan view of the site being investigated on the first day of the investigation showing existing and proposed structure lines as well as the traces of contamination visible on the surface (heavy curved lines), sampling locations (small, lighter shaded, squares) and the estimated area of contamination (lighter, curved lines)

The subject invention provides an integrated system and process that insures a low cost, high quality, rapid timeline environmental field screening. It is the unique combination of components and the rapid iterations that contributes to the invention. The preferred components of the integrated system include:

(1) Intrusive sampling based on (but not limited to) "push" technology for surface, subsurface and groundwater media sampling.

(2) Field mobile laboratory equipped to complement expected site contaminants.

(3) Computer assisted design/geographical information system (CAD/GIS) data management with interactive three dimensional dynamic graphs presentation capability.

(4) Global positioning system (GPS) for sample coordinates determination.

(5) Telecommunication linkup for data transmittal and receiving.

Using the above components in an integrated fashion, the inventive environmental screening system is designed to determine the horizontal and vertical extent of site soil and/or groundwater contamination with the mobilization of the field investigative team. The system allows for making informed field change decisions concerning site investigation plans on a real time basis, thus assuring minimum field time, minimum cost, and maximum data quality.

The uniqueness of the invention is the unexpected results that occur with the integration of the noted components in concert with rapid process iterations. No one component impacts results to the degree that occurs with the integrated system. The results exceed the sum of the parts. Conventional environmental field screening procedures are sequenced as follows. The sample is taken from a gridded plan by some intrusive means, the sample is sent to a analytical laboratory, the results are made known, the sampling locations are surveyed in, and an analysis is made of the data. The result is a lengthy process, that is expensive, requires excessive sampling handling, and has been shown to be of questionable quality. By integrating each of these steps into single system, the time line has been cut by 60%, the cost by 70%, and the probability of accurately determining the existence of the environmental problem has increased by five fold. For example, the FAST system has a feedback before the placement of the next well, thus optimizing well placement. This leads to the reduction in data points necessary to characterize the site and, ultimately the elimination of the need for a Phase II investigation.

The preferred components of the inventive system include:

1. The intrusive sampling system—the unit of choice is the GEOPROBE® (manufactured by Kejr Engineering, Inc. of Salinas, Kans.) or similar machine having the following basic specifications:

The unit is a self contained, motorized, hydraulic powered probe unit operated from a hydraulic system driven from the vehicle motor or an auxiliary engine.

The probe unit folds for transport and is capable of being set up in seconds. It uses static force (weight of vehicle) and percussion to advance the probing tool.

The unit drives small diameter (1.0" O.D. to 1.6" O.D.) probing tools to depth.

Figure 8:
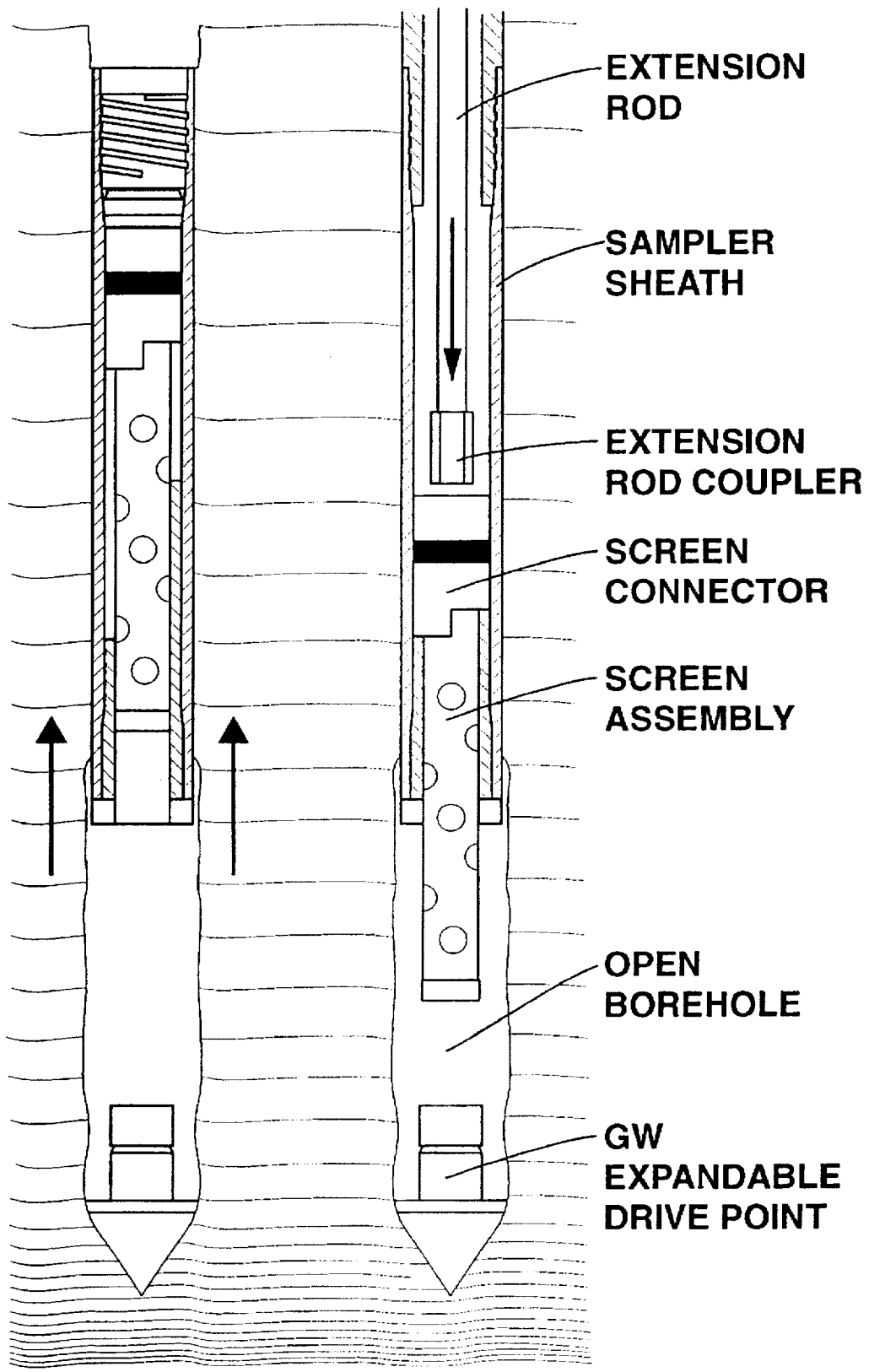
FIG. 8 is a side view of a sampling subsystem suitable for use with the present invention.

As shown in FIG. 8, a typical sampler may be operated by being driven to the desired sampling depth (while sealed by o-ring connections placed at critical locations on the assembly). When the desired sampling depth is reached, the sampler is preferably pulled up about 2 feet which disengages the expendable drive point and creates an open borehole from which to sample. The inner core, which consists of a stainless steel wire screen inside of a perforated stainless steel sleeve, in then pushed out into the borehole and water is allowed to enter the sampler. A groundwater sample can then be collected. Push-probes of this general type are able to sample in approximately 70 percent of U.S. soils. In other circumstances, or if desired, suitable sampling may also be accomplished with augers or other means.

Figure 9:
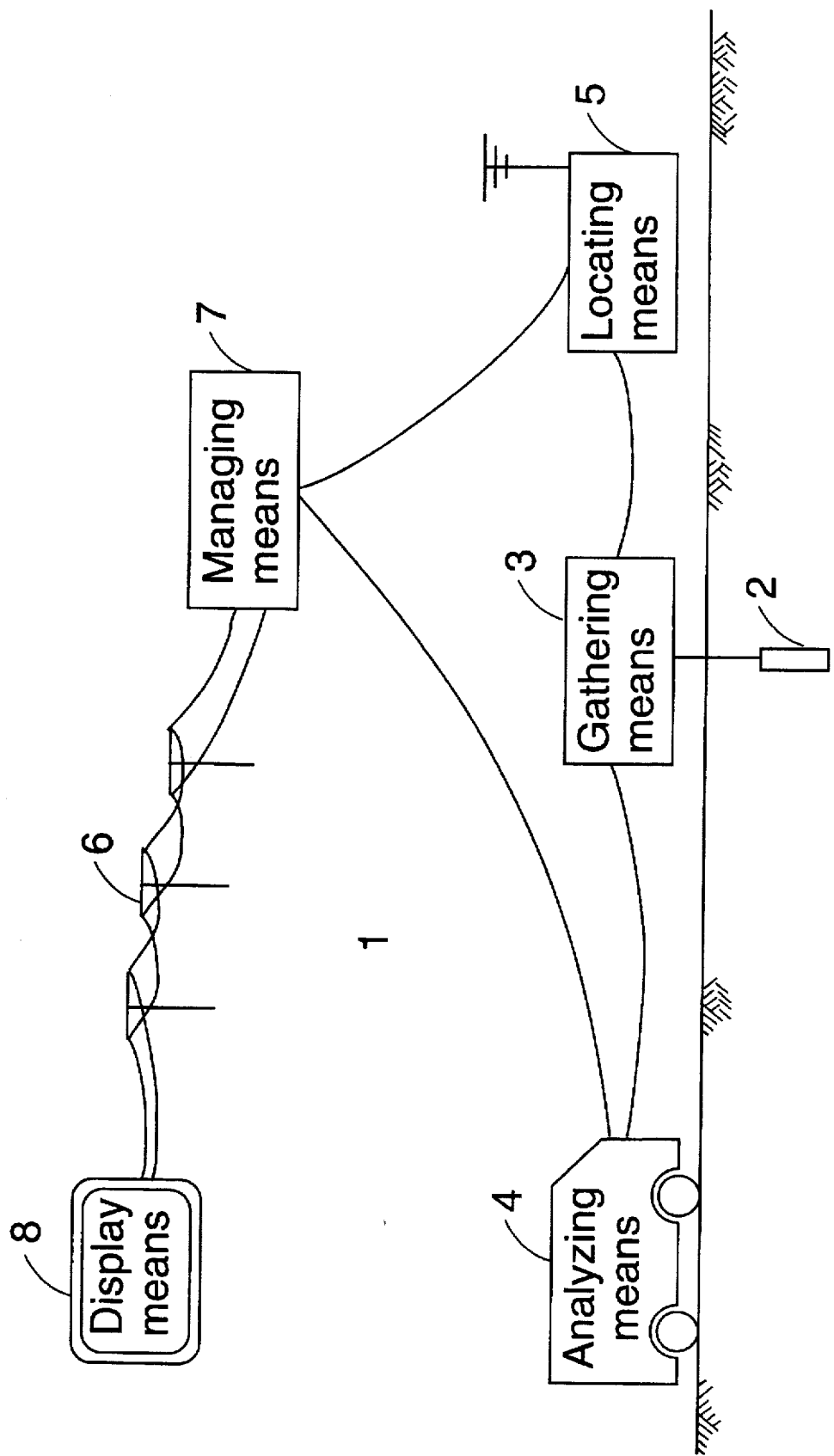

FIG. 9 shows a block diagram describing integrated system according to the present invention. In FIG. 9, an integrated system (1) for gathering, processing, and reporting data relating to soil, groundwater or other contamination of a site (ground) comprises means (2) for probing the subsurface of the site, shown below ground; means (3) for gathering samples of the subsurface material, shown above the Found surface; means (4) for analyzing the samples; means (5) for locating the origin of the samples; means (6) for transmitting the data generated by the analyzing means; means (7) for managing the data from the locating means and the analyzing means for projecting and forwarding the next probable location to a display; and means (8) for displaying the data.

Figure 10:
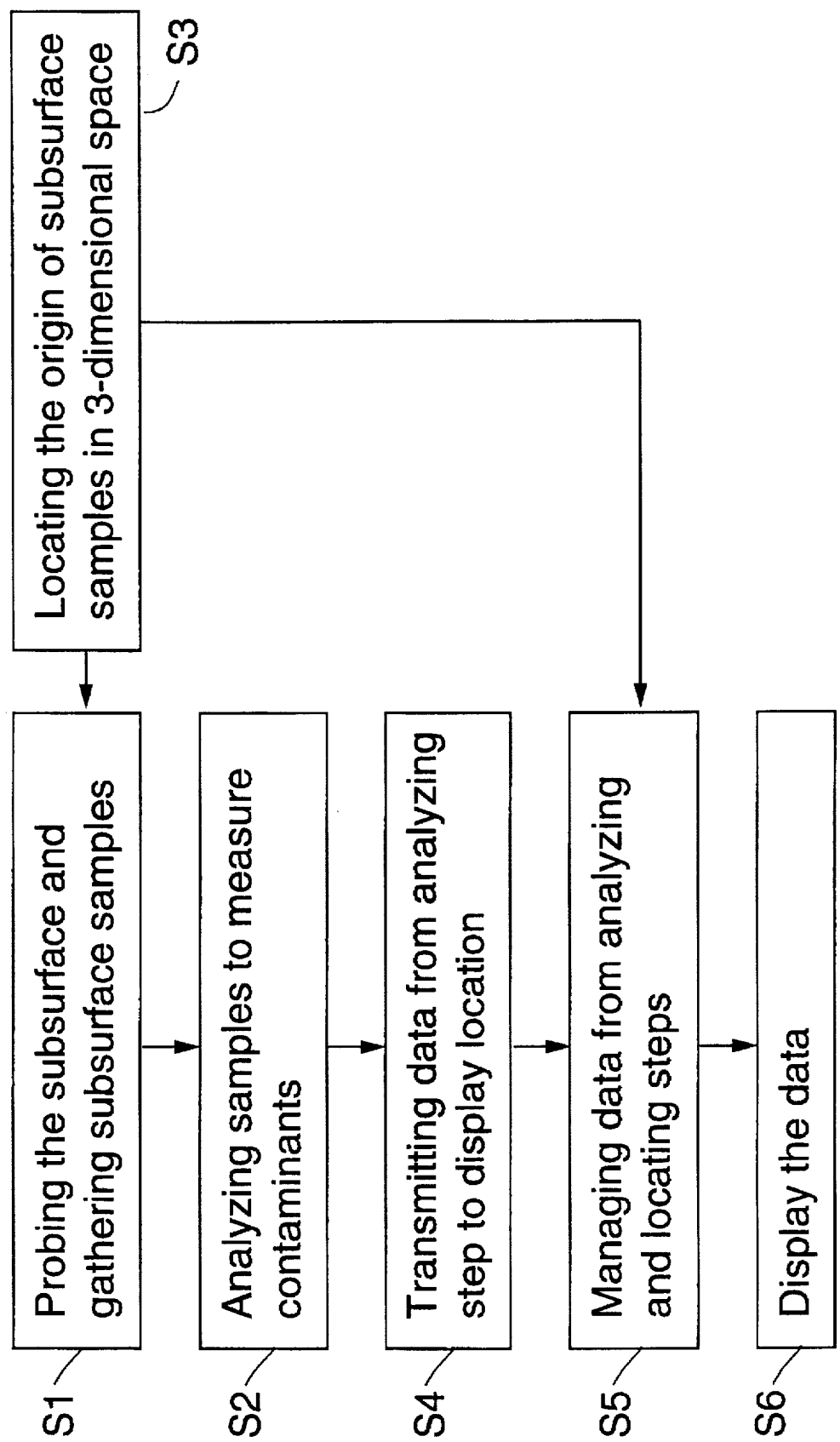
FIG. 10 is a flow chart describing the different steps performed by the method of the claimed invention.

FIG. 10 shows a flow chart describing the different steps performed by the method according to the present invention. In FIG. 10, a process for gathering, processing, and reporting data relating to soil, groundwater or other contamination of a site (ground) comprises the steps of probing (S1) the subsurface of the site, including gathering samples of the subsurface material; analyzing (S2) the samples to measure contaminants therein; locating (S3) the origin of the samples in three-dimensional space; transmitting (S4) the data generated by the analyzing step to a location for display; managing (S5) the data from analyzing the samples and the data from locating the origin of the samples to project the next probable sample location and to forward the next probable sample location for use as a guide in the placement of ensuing sample locations; and displaying (S6) the data the data at the display location, all the steps being arranged to work together iteratively, whereby the number of samples needed to accurately characterize the site is minimized.

2. The field laboratory—the contents of this unit are determined by the analytical requirements at the investigation site. Typically this unit contains, but is not limited to, a gas cromatrograph, sometimes coupled with a mass spectrograph, a metals detecting system such as an x-ray fluorescence system, and other analytical systems as needed (i.e., sufficient materials and equipment to analyze samples for volatile organic compounds pursuant to method EPA 8240). A preferred unit is the Hewlett Packard Model HP 5890 Series II gas chromatograph, more preferably, one equipped with a 5971 series mass-selective detector (or mass spectrometer) and an electron capture detector. Each of these systems downloads to an onboard computer that records and stores the developed analytical information.

3. The surveying system—the unit of choice is a Ground Positioning System (GPS) manufactured by Ashtech (of Sunnyvale, Calif.). This system electronically surveys the surface position of the sample point on the X, Y, and Z axes using the sample's position relative to various satellites. The survey information is also downloaded into the field laboratory computer.

4. The data management system—on an as needed basis, the stored analytical and survey/information is downloaded, either by cellular phone or hard wire phone, to a CAD/GIS system. Preferred data management software is produced by Schreiber Instruments, Inc. of Denver, Colo. Preferable, because of the data flow rates utilized, a hard wire phone system is used to transmit the data. This system then visually presents the downloaded data, (see, e.g., FIGS. 1-7) and subsequently projects, if requested, the next probable sample location. This information is forwarded back to the field laboratory and used as a guide in the placement of the ensuing sample locations.

EXAMPLE

To better understand the inventive process and apparatus the following example is submitted. While technically accurate, the example uses generalized data in order to avoid disclosing confidential information about any particular site. Background:

A hypothetical military bases has been in continuous operation since 1946. During this time period this military operation has conducted maintenance on numerous military vehicles. Chlorinated solvents (TCE) have long been used to degrease engine parts. Over the years, quantities of the chlorinated solvent have been spilled.

The hypothetical military base is located in the Coastal Plain physio-graphic province. The Coastal Plain consists of a seaward thickening accumulation of sediments overlying a basement complex of igneous and metamorphic rocks. The surficial sediments at the base consist predominantly of sands of Pliocene to Recent age. These unconsolidated deposits extend from the land surface of −40 to −8 feet elevation.

The primary source of potable groundwater is the Floridan aquifer, composed primarily of limestone formations. The aquifer immediately being threatened by contamination is the unconfined surficial aquifer. While this limestone aquifer has not been significant as a potable water source, it is now being considered as an alternate water source to relieve the demand on the principal aquifer.

Before beginning the site characterization effort using the inventive FAST method, parameters must be decided upon for several factors. For example, contaminant-specific action levels must be selected. In the present example, 5 ppb of TCE was selected as the lower threshold for monitoring the contamination. This limit was chosen to fall in line with the applicable relevant and appropriate requirements (ARAR) in the area. In passing, it is also noted that the usage of the FAST technology is especially well suited to the Data Quality Objectives Process for Superfund—EPA/540/G-93-071.

The components used to conduct the inventive FAST process comprise a Perma-Screen (a GEOPROBE® inserted into a fully packed 1-in. stainless steel well) for acquiring groundwater samples. These wells would be allowed to remain in place for use as preliminary future monitoring points. The method of analysis is a gas chromatograph (GC) with second column configuration using a Halls detector. A second GC is used to confirm analytical results. All analysis work is accomplished in an on-site field laboratory. Location of samples is done through use of the GPS (Geographic Positioning System) system made by Ashtech, Inc. The data was displayed through use of the mapping software and equipment sold by Schreiber Instruments, Inc.

Results of the Investigation:

The following discussion and FIGS. 1-7 summarize the findings of a 6-day field effort. At the end of the project the delineation of the groundwater contamination having as its source the motor vehicle maintenance area is complete. The plume has been bounded in all three dimensions and its characterization is complete. At any given time, the field manager has the option to segmentize the plume according to concentration to isolate levels of contamination thus showing the "hot" spots.

Day One—Four Sample Locations—FIG. 1:

The FAST technology uses an iterative process to establish the boundaries and the characteristics of the TCE plume. FIG. 1 represents the first day of intrusive sampling shown in plan view. Four sampling locations were selected in the immediate area of the spill site (shown in FIG. 1 by small, light squares within contaminated-dark area). Three samples from each location were taken at varying depths. All twelve samples were analyzed in the adjacent on-site field laboratory. The analytical results were imaged according to their respective spatial locations. Based only on these twelve points, the model deemed the area of contamination to be 8,183,434 cubic feet in volume.

Figure 2:
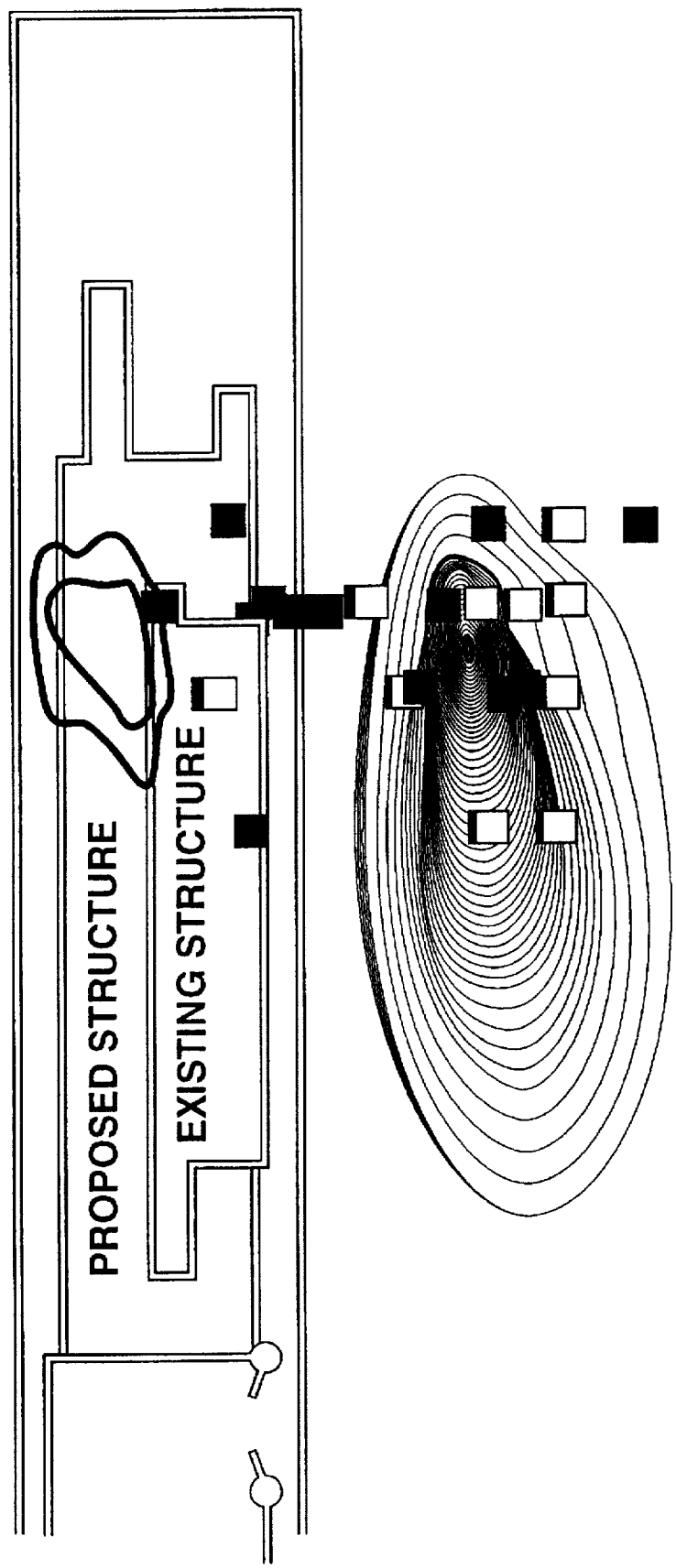
FIG. 2 is a side view in cross-section of the site on the second day of the investigation showing the estimated area of contamination segmented according to level of contamination, the sampling locations are shown as darker squares.

Day Two—Nine Sample Locations Total (Five New)—FIG. 2:

FIG. 2 includes a visual representation of the findings from the first day of intrusive sampling. This data allowed the field manager to select the next five intrusive sampling locations, using the visual representation to confirm or deny the existence of the plume of contaminant based on the information developed in the first four probes. The principal effort of all ensuing days of fieldwork was to determine the boundaries of the contaminant in real time.

Figure 3:
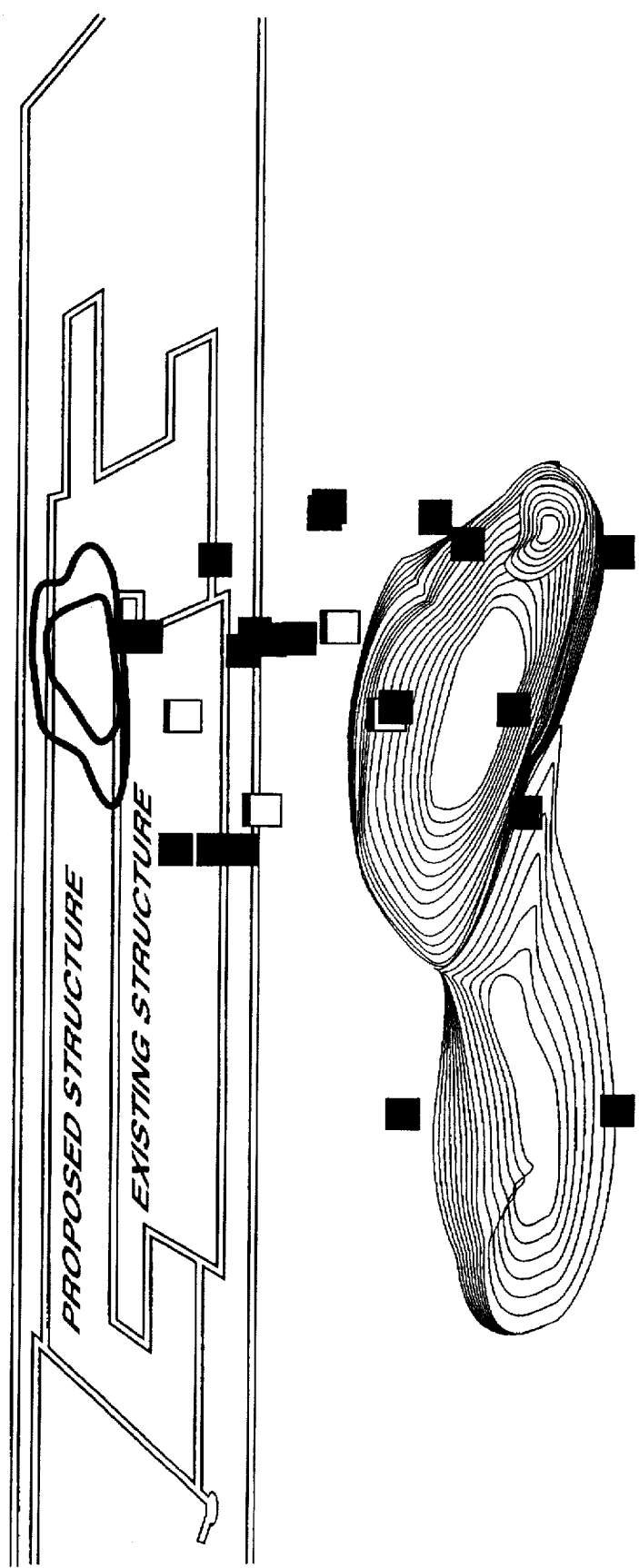
FIG. 3 is a side view of the site on the third day of the investigation.

Day Three—Fourteen Sample Locations Total (Five New)—FIG. 3:

The samples taken in day three show that a portion of the plume has been bounded; however, further delineation of the plume upgradient and downgradient of the spill point should be determined. The lower limits of the plume have been established.

In this regard, background information may also help to direct subsequent sampling. For example, by knowing the predominant liquid flow direction and speed of the contaminant, the geology of the area (e.g., permeability, faults, etc.), and/or the contaminant's characteristics (e.g., benzene has a tendency to float on top of other components; on the other hand, TCE sinks into the aquifer) can all also help in more efficiently selecting sampling locations.

Figure 4:
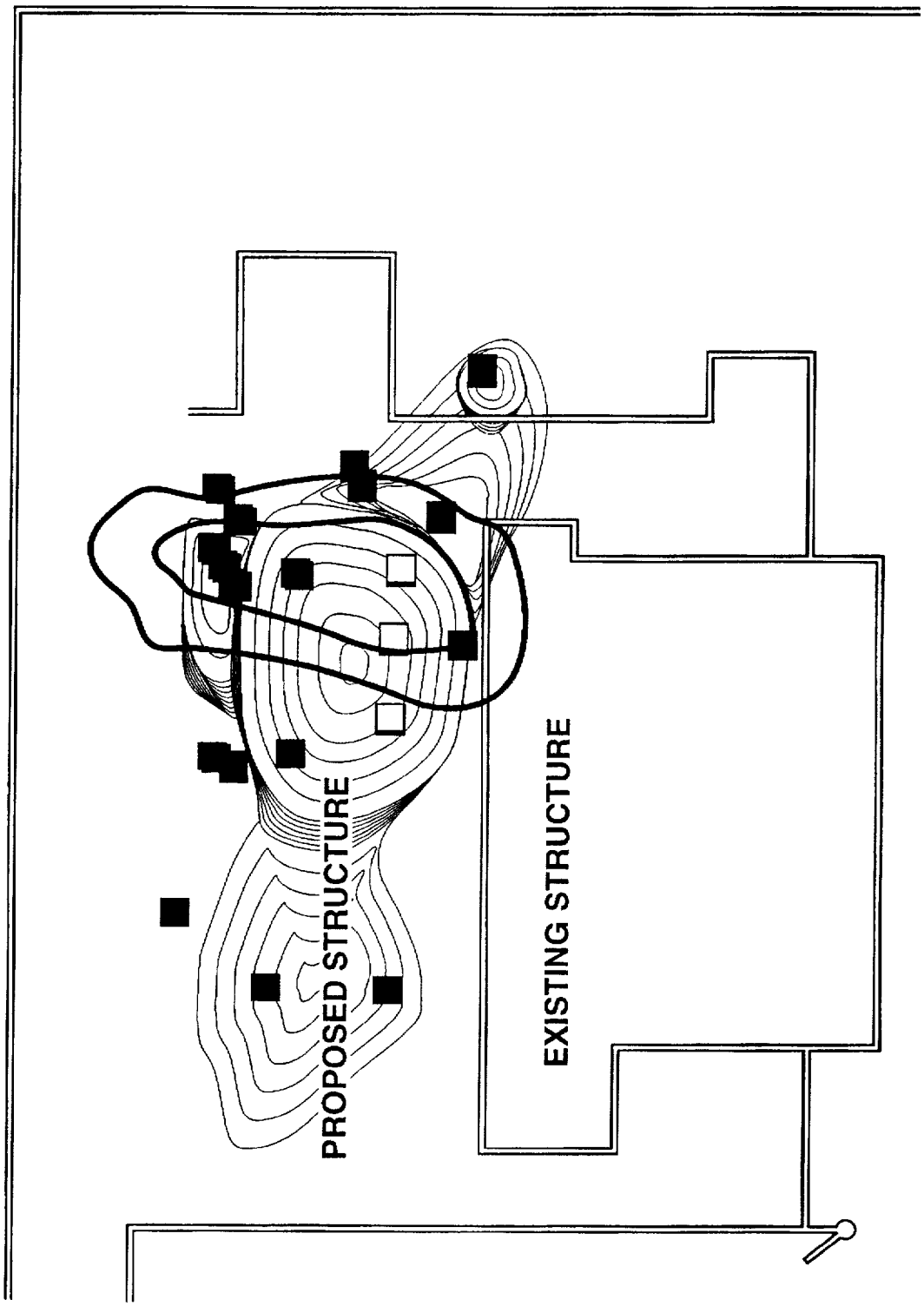
FIG. 4 is a plan view of the site on the fourth day of the investigation.

Day Four—Eighteen Sample Locations Total (Four New)—FIG. 4:

Plume bounding continued on day four based on the outcome of the results shown from the effort of the previous day. Both extremes of the leading edge of the plume have been established.

Figure 5:
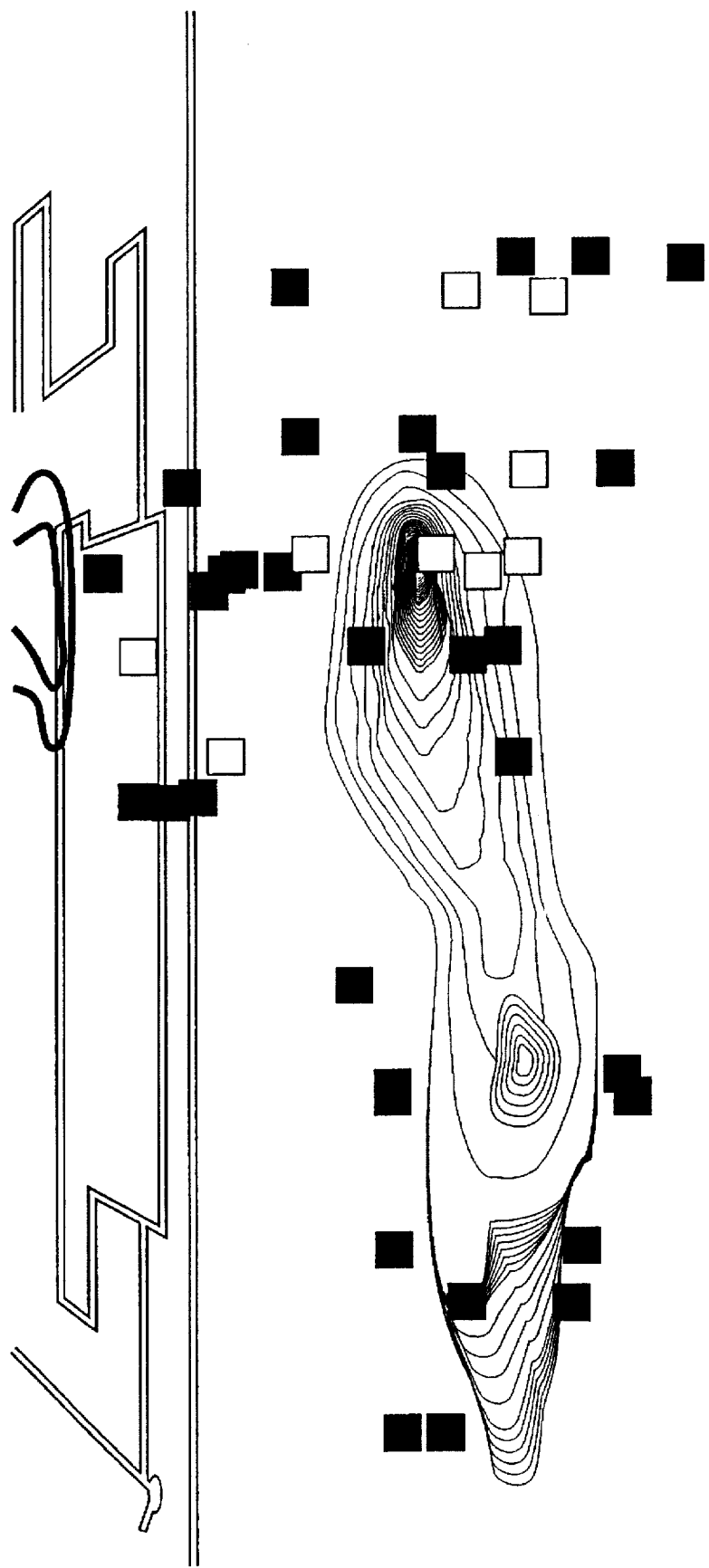
FIG. 5 is a side view in cross-section of the site on the fifth day of the investigation.

Day Five—Twenty-Two Sample Locations Total (Four New)—FIG. 5:

Refinement of the boundaries of the plume were continued on day 5. Most of the effort was directed at free tuning plume dimensions.

Figure 6:
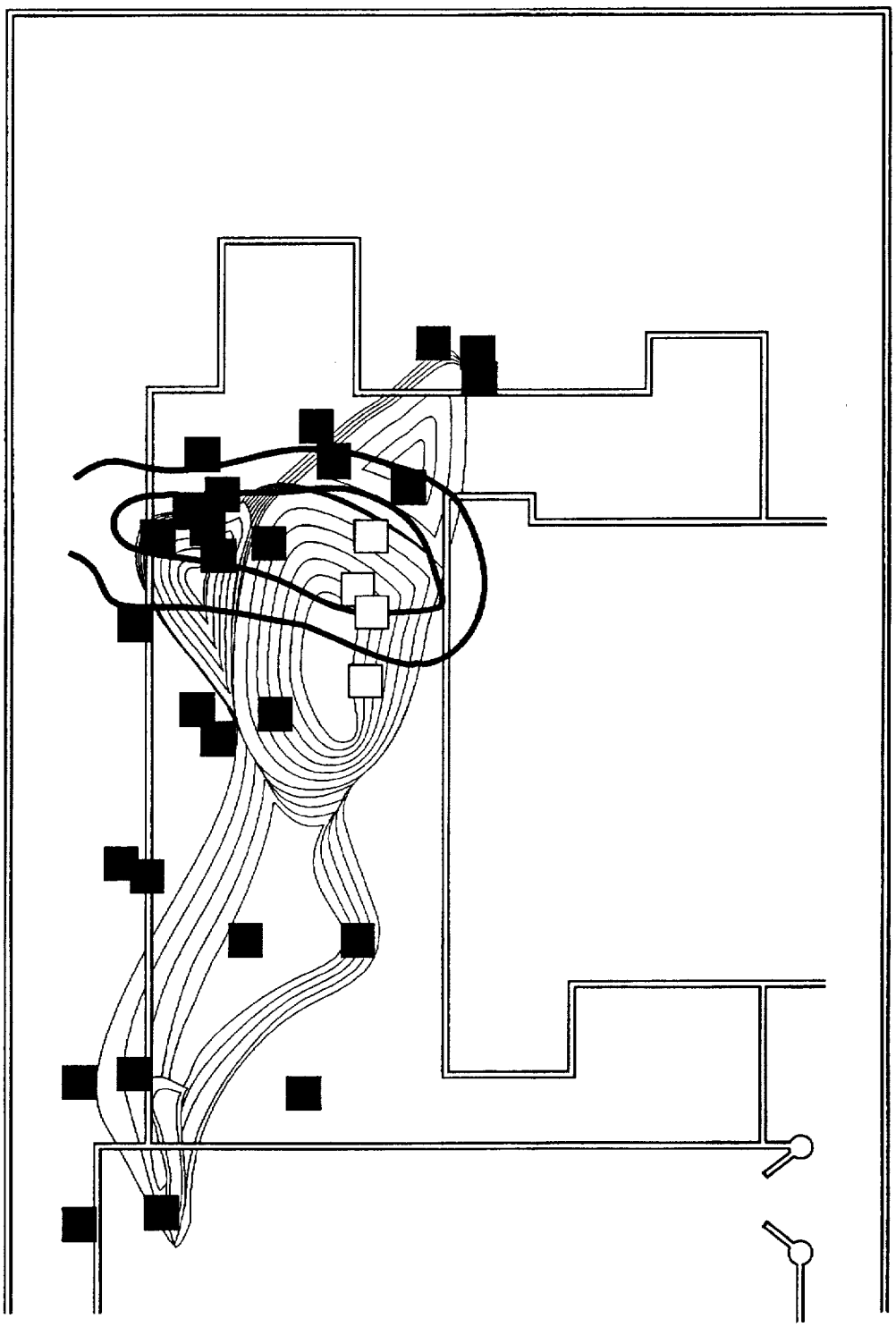
FIG. 6 is a plan view of the site on the sixth, and final, day of the investigation.
Figure 7:
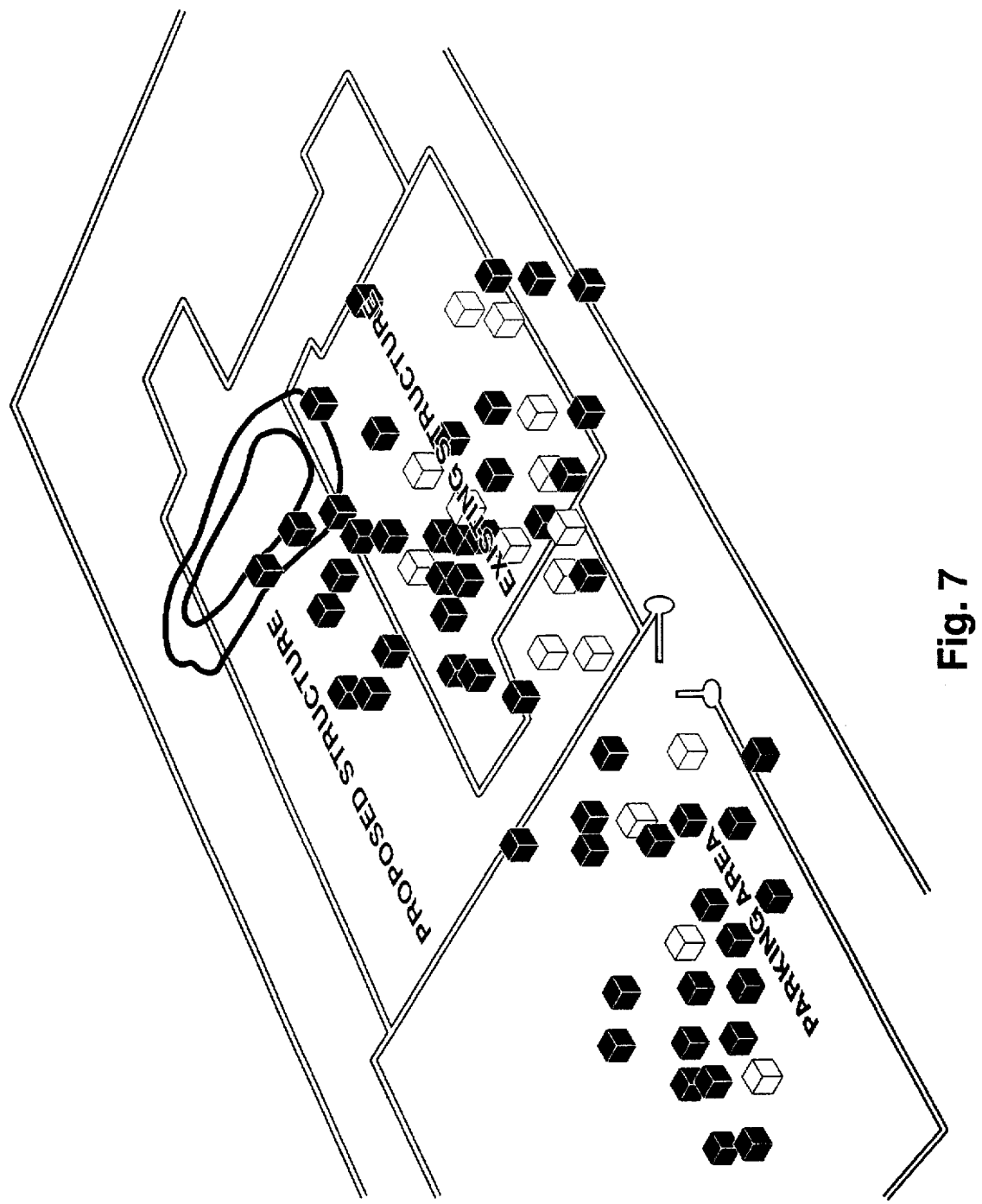
FIG. 7 is perspective view of the site under investigation showing all 72 samples (i.e., twenty-four locations with three samples each), TCE contamination is shown by dark squares.

Day Six—Twenty-Four Sample Locations Total (Two New)—FIGS. 6 and 7:

Two additional sample locations were selected for final definition of the plume toe. The sum of these twenty-four sample locations shows that the plume is fully bounded. The calculation of the plume dimension shows the area of contamination to be 1,624,989 cubic feet in size. This is less than one fifth of the initial estimate of contaminated area. Since the cost to simply remove dirt is upwards of $10 per crane-shovel load (about a cubic yard) (to say nothing of the costs associated with storing contaminated soil—or of trucking in uncontaminated soil) the savings associated with this increase in accuracy mount very quickly.

The efficiencies and exactness provided by the inventive FAST system are visible by comparing the various figures. The estimated area of contamination becomes progressively smaller and more exactly defined. Also, the sampling is vastly more efficient compared to the prior art "grid" methods. FIG. 7 shows that through the inventive iterative process some areas were sampled heavily whereas others could be abandoned as soon as it was shown that contamination did not extend that far.

As will be understood by those skilled in the relevant are to which the invention pertains, the preceding description and examples are intended as representative only, and should not be viewed as limiting the invention, which is delineated only by the appended claims.

What is claimed is:

1. An integrated system for gathering, processing, and reporting data relating to soil, groundwater or other contamination of a site comprising:

(a) means for probing the subsurface of a site, including means for gathering samples of the subsurface material;

(b) means for analyzing said samples to measure contaminants therein, said analyzing means generating data characteristic of said site;

(c) means for locating the origin of said samples in three-dimensional space;

(d) means for transmitting the data generated by said analyzing means to a location for display thereof;

(e) means for managing the data generated by said means for locating and said means for analyzing said means for managing of projecting the next probable sample location and forwarding the next probable sample location for use as a guide in the placement of ensuing sample locations; and (f) means for displaying the data at said display location, said probing, analyzing, locating, transmitting, analyzing, and displaying means being arranged to work together iteratively, whereby the number of samples needed to accurately characterize said site is minimized.

2. The integrated system of claim 1, wherein said probing means for gathering samples comprises a push probe.

3. The integrated system of claim 1, wherein said analyzing means comprises a mobile laboratory.

4. The integrated system of claim 1, wherein said locating means comprises a satellite ground positioning system.

5. The integrated system of claim 1, wherein said display means comprises a computer program for generating images of said site and images of said contamination within said site.

6. The integrated system of claim 1, wherein said means for managing comprises a computer program and system.

7. An integrated system for gathering, processing, and reporting data relating to soil, groundwater, or other contamination of a site comprising:

(a) a probe for gathering subsurface samples;

(b) a mobile laboratory for analyzing said samples; and generating data reflecting said analysis;

(c) a satellite location system for placing said samples in three-dimensional space;

(d) a telephone line for transmitting said data;

(e) a computer program and system for managing the data generated by said mobile laboratory and said satellite location system, said computer program of projecting the next probable sample location and being capable of forwarding the next probable sample location for use as a guide in the placement of ensuing sample locations; and (f) a computer program and system for displaying said data;

said probe, mobile laboratory, satellite location system, telephone line, and computer programs and systems being arranged to work together iteratively, whereby the number of samples needed to accurately characterize said site is minimized.

8. A process for gathering, processing, and reporting data relating to soil, groundwater or other contamination of a site comprising the steps of:

(a) probing the subsurface of a site, including gathering samples of the subsurface material;

(b) analyzing said samples to measure contaminants therein;

(c) locating the origin of said samples in three-dimensional space;

(d) transmitting the data generated by said analyzing step to a location for display;

(e) managing the data from analyzing the samples and the data from locating the origin of the samples to project the next probable sample location and to forward the next probable sample location for use as a guide in the placement of ensuing sample locations; and (f) displaying said data at said display location, said steps (a–f) being arranged to work together iteratively, whereby the number of samples needed to accurately characterize said site is minimized.

9. The process of claim 8, wherein said probing for sampling step is accomplished by a push probe.

10. The process of claim 8, wherein said analyzing step is accomplished by a mobile laboratory.

11. The process of claim 8, wherein said locating step is accomplished by a satellite system.

12. The process of claim 8, wherein said display step is accomplished by a computer program for generating images of said site.

13. The process of claim 8, wherein said managing step is accomplished by a computer program and system.

* * * * *